United States Patent [19]
Hahnen et al.

[11] Patent Number: 5,586,990
[45] Date of Patent: Dec. 24, 1996

[54] ENDOSURGICAL INSTRUMENT WITH A RADIALLY MOVABLE END EFFECTOR

[75] Inventors: Kevin F. Hahnen, Miami; Laszlo Farkas, Hialeah, both of Fla.; David P. Gordon, Stamford, Conn.

[73] Assignee: Symbiosis Corporation, Miami, Fla.

[21] Appl. No.: 436,121

[22] Filed: May 8, 1995

[51] Int. Cl.⁶ .................................................. A61B 17/32
[52] U.S. Cl. .................................... 606/170; 606/167
[58] Field of Search .................................. 606/159, 170, 606/171, 167

[56] References Cited

U.S. PATENT DOCUMENTS

| | | |
|---|---|---|
| 2,668,537 | 2/1954 | Kapp . |
| 4,729,374 | 3/1988 | Alfranca . |
| 4,963,147 | 10/1990 | Agee et al. ............................. 606/170 |
| 5,053,044 | 10/1991 | Mueller et al. ......................... 606/159 |
| 5,069,679 | 12/1991 | Taheri ..................................... 606/159 |
| 5,089,000 | 2/1992 | Agee et al. ............................. 606/170 |
| 5,112,346 | 5/1992 | Hiltebrandt et al. .................... 606/170 |
| 5,152,772 | 10/1992 | Sewell, Jr. ........................ 606/170 X |
| 5,282,813 | 2/1994 | Redha ..................................... 606/159 |
| 5,403,328 | 4/1995 | Shallman ................................ 606/144 |
| 5,443,475 | 8/1995 | Auerbach et al. ...................... 606/170 |

*Primary Examiner*—Michael Powell Buiz
*Assistant Examiner*—Patrick W. Rasche
*Attorney, Agent, or Firm*—David P. Gordon

[57] ABSTRACT

An endosurgical cutting instrument includes a hollow tube having a distal end with a radial slot and an interior deflection surface, a push rod extending through the tube and having a proximally directed sickle blade coupled to its distal end, and a manual actuator coupled to the proximal ends of the tube and the push rod for imparting relative axial movement to the tube and push rod. The sickle blade is a curved member having a sharp concave edge and a dull convex edge and is coupled to the distal end of the push rod with its sharp concave edge facing the push rod. The blade is dimensioned such that it may be substantially completely contained within the tube. The push rod is oriented so that its distal end is free to move in a radial direction as it moves axially. Movement of the push rod against the deflection surface urges the push rod in a radial direction thereby causing the sickle blade to exit the tube through the radial slot. As the sickle blade is moved out of the tube, there is no cutting action since it is the dull convex edge of the blade which faces the tissue adjacent to the tube. Once the blade is deployed outside the tube, cutting is effected by capturing tissue in the space between the concave cutting edge of the blade and the exterior of the tube.

20 Claims, 5 Drawing Sheets

ENDOSURGICAL INSTRUMENT WITH A RADIALLY MOVABLE END EFFECTOR

BACKGROUND OF THE INVENTION

1. Field of the Invention

This invention relates broadly to endosurgical instruments. More particularly, this invention relates to an endosurgical instrument having an end effector which is radially movable.

2. State of the Art

Endoscopic surgery is widely practiced throughout the world today and its acceptance is growing rapidly. In general, endoscopic/laparoscopic surgery involves one or more incisions made by trocars where the trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, an organ or tissue may be grasped with one surgical instrument and simultaneously cut with another surgical instrument while under the observation of the surgeon via the optical instrument in place in the trocar tube.

Various types of endoscopic surgical instruments are known in the art. These instruments generally include a slender tube containing a push rod which is axially movable within the tube by means of a manual actuator. One or more end effectors are coupled to the distal ends of the tube and the push rod so that axial movement of the push rod is translated to rotational or pivotal movement of the end effector(s). End effectors may take the form of scissors, grippers, cutting jaws, forceps, and the like. Endosurgical scissors usually include a pair of scissor elements (blades) attached to each other or a clevis by a pivot axle. These scissors may be single acting or double acting. In a single acting scissors, a first scissor element is held stationary relative to the distal end of the tube and a second scissor element is rotated about the pivot axle relative to the first scissor element. Endosurgical scissors are available in many forms, e.g. curved blades, hooked blades, angled blades, etc. However, most endosurgical scissors have relatively sharp distal ends and cut in the distal direction. These common design features of most endosurgical scissors present two disadvantages: (1) when locating the scissor blades at the surgical site, tissue may inadvertently be punctured or scarred by the sharp distal ends of the blades; and (2) since the endoscope and the scissors typically approach the surgical site from substantially the same direction, it is often difficult to see the tissue which is cut distally from the scissor blades. These disadvantages become quite problematic when the endosurgical cutting instrument is used in the vicinity of very delicate tissues such as the arachnoid membrane of the meninges.

Endosurgical grippers and forceps are similar in design to endosurgical scissors, but with a pair of gripping elements rather than a pair of scissor blades. The common design features of endosurgical grippers, forceps, and scissors present the disadvantage that they grip or cut in a distal direction. This tends to push the subject tissue away from the instrument which results in a possible failure to cut or grip the tissue.

U.S. Pat. Nos. 4,963,147 and 5,089,000 to Agee et al. partially address the problems encountered with conventional endosurgical cutting instruments. Both of these patents disclose a surgical instrument for the treatment of carpel tunnel syndrome. The cutting instrument disclosed by Agee et al. includes a hollow tube having a radial slit and a single cutting blade which is movable into and out of the radial slit by a push rod. The distal end of the tube is provided with a slotted rotatable pivot member through which the cutting blade is translated and rotated. In use, the cutting blade exits the radial slot in the tube with its sharp point angled in the distal direction and its cutting edge forming an obtuse angle with the proximal portion of the tube. The pivot member allows the blade to rotate slightly in the proximal direction as it exits the tube. The instrument is fairly complex and cutting is effected in a direction away from the tube. Thus, as the cutting blade is moved out of the tube, any tissue adjacent to the radial slot in the tube is exposed to the sharp point and cutting edge of the cutting blade.

A similar device is disclosed in U.S. Pat. No. 5,053,044 to Mueller et al. which concerns a cardiovascular catheter having a blade tip capable of making a radial incision. The blade is mounted inside the tip of the catheter and is rotatable out of the tip through a radial slot. Cutting is effected in a radially outward direction.

It is known to provide an endosurgical cutting instrument which cuts in the radially inward direction. These instruments are sometimes referred to as "retrograde" cutting instruments. U.S. Pat. No. 4,729,374 to Alfranca discloses a surgical instrument for transcholedochal papillotomy which includes a flexible coil with a single acting retrograde scissor end effector coupled to its distal end and a pull wire extending through the coil and coupled to the end effector. The end effector includes a fixed blade coupled to the distal end of the coil and having a blunt distal end and a movable blade distally hinged to the fixed blade. The distal end of the pull wire is coupled to the movable blade by a connecting rod which is hingedly connected to both the pull wire and the movable blade. A proximal handle with a displaceable spool moves the pull wire through the coil to open and close the movable blade. While the instrument may be effective in performing a retrograde cutting operation, it is mechanically complex and difficult to manufacture.

U.S. Pat. No. 5,112,346 to Hiltebrandt et al. discloses a retrograde cutting hook punch having a hollow tube with a push rod extending through it and a single acting end effector coupled to the distal ends of the tube and the push rod. The end effector includes a stationary member which is coupled to the distal end of the tube and a movable member which is distally hinged to the stationary member and hingedly coupled to the distal end of the push rod. The cutting hook punch is designed specifically for arthroscopic procedures and has a complex geometry. Like the cutting instrument disclosed by Alfranca, the cutting hook punch has at least two hinged couplings.

SUMMARY OF THE INVENTION

It is therefore an object of the invention to provide an endosurgical cutting instrument which presents no sharp points or edges while being located at the surgical site.

It is another object of the invention to provide an endosurgical cutting instrument which cuts in a direction that is easily viewable through an endoscope.

It is also an object of the invention to provide an endosurgical cutting instrument which minimizes the possibility of inadvertently cutting tissue which is radially or distally adjacent to the surgical site.

It is a further object of the invention to provide an endosurgical cutting instrument which cuts in a radially inward and/or proximal direction.

It is another object of the invention to provide an endosurgical gripping instrument which grips in a radially inward direction.

It is also an object of the invention to provide an endosurgical instrument which does not utilize hinged or pivotal couplings at the end effector.

It is another object of the invention to provide an endosurgical instrument which has few moving parts and is inexpensive to manufacture.

In accordance with the objects, which will be discussed in detail below, an endosurgical cutting instrument according to the invention generally includes a hollow tube having a distal end with a radial slot and an interior inclined deflection surface, a push rod extending through the tube and having a proximally directed sickle blade coupled to its distal end, and a manual actuator coupled to the proximal ends of the tube and the push rod for imparting relative axial movement to the tube and push rod. The sickle blade is a curved member having a sharp concave edge and a dull convex edge and is coupled to the distal end of the push rod with its sharp concave edge facing the push rod. In addition, the sickle blade is dimensioned such that it may be substantially completely contained within the diameter of the hollow tube. The push rod is oriented so that its distal end is free to move in a radial direction as it moves axially. The inclined deflection surface is preferably arranged at the distal end of the tube such that axial movement of the push rod against the deflection surface urges the push rod in a radial direction (i.e. up the inclined deflection surface) thereby causing the sickle blade to exit the tube through the radial slot. As the sickle blade is moved out of the tube through the radial slot, there is no cutting action since it is the dull convex edge of the blade which faces the tissue adjacent to the tube. Once the blade is deployed outside the tube, cutting is effected by capturing tissue in the space between the concave cutting edge of the blade and the exterior of the tube. When tissue is thus captured, cutting may be effected in a radial direction by proximal axial movement of the push rod which draws the blade back into the tube, and cutting may be effected in a proximal direction by proximal movement of the entire cutting instrument with the blade deployed.

The cutting instrument according to the invention is therefore atraumatic at all times prior to the actual cutting operation. The instrument is directed to the surgical site with the cutting blade contained within the tube and the cutting blade is deployed without exposing its sharp edge to adjacent tissue.

According to a preferred embodiment of the invention, the deflection surface is formed as a substantially cylindrical inclined passage and the distal end of the push rod is provided with a piston-like member which rides in and is guided by the passage.

According to other aspects of the invention, clamping and/or dissecting instruments utilizing the inclined deflection surface of the invention are also provided. The clamping and dissecting instruments include forward acting and retrograde instruments.

Additional objects and advantages of the invention will become apparent to those skilled in the art upon reference to the detailed description taken in conjunction with the provided figures.

DETAILED DESCRIPTION OF THE PREFERRED EMBODIMENTS

Turning now to FIGS. 1–5, an endosurgical cutting instrument 100 according to the invention generally includes a hollow tube 102, a push rod 104 extending through the hollow tube, a proximal handle actuator 106 coupled to the proximal ends of the tube and push rod, and a sickle cutting blade 108 coupled to the distal end of the push rod 104. The distal end of the tube 102 is provided with a radial slot 110 and an inclined distal deflecting surface 112. The proximal handle actuator 106 includes a handle portion 114 which is coupled to the proximal end of the tube 104 and a lever portion 116 which is coupled to the proximal end of the push rod 104. In addition, the lever portion 116 is rotatably coupled to the handle portion 114 by a pivot axle 118. Rotation of the lever portion 116 relative to the handle portion 114 results in axial movement of the push rod 104 relative to the tube 102. Those skilled in the art will appreciate that the proximal end of the push rod 104 is preferably coupled to the lever 116 by a ball and socket or disk and socket coupling 117 as described more fully in co-owned U.S. Pat. No. 5,174,300, the complete disclosure of which is incorporated herein by reference. As will be better understood from the discussion which follows, axial movement of the push rod 104 relative to the tube 102 results in a non-rotational radial movement of the cutting blade 108 in or out of the radial slot 110.

Figure 3:
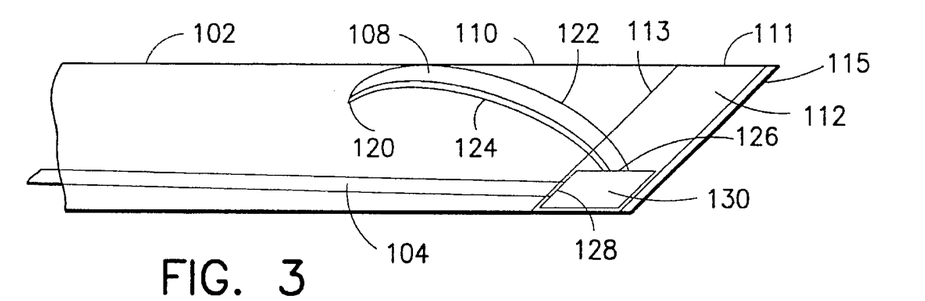
FIG. 3 is a broken enlarged partially transparent view of the distal end of the endosurgical instrument of FIGS. 1 and 2 with the cutting blade in the retracted position.
Figure 4:
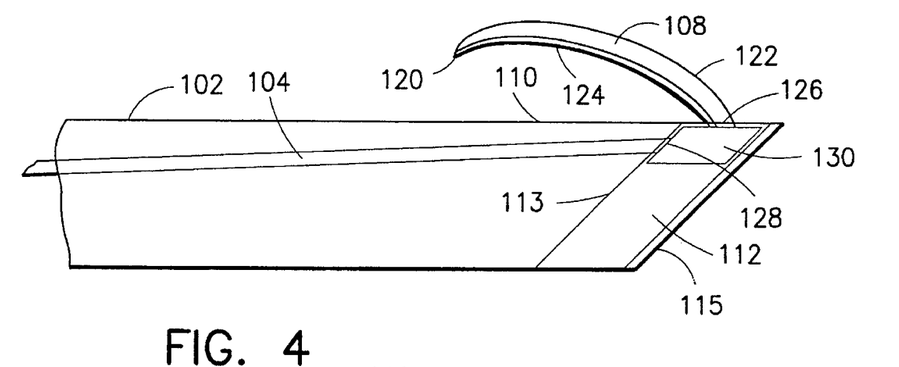
FIG. 4 a broken enlarged partially transparent view of the distal end of the endosurgical instrument of FIGS. 1 and 2 with the cutting blade deployed.
Figure 5:
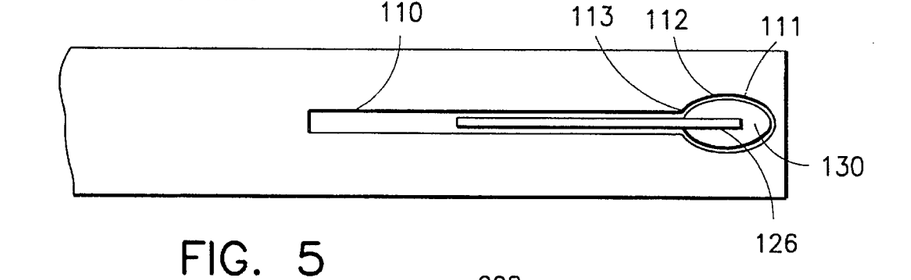
FIG. 5 is a broken enlarged top plan view of the distal end of the endosurgical instrument of FIGS. 1 and 2 with the cutting blade deployed.

As seen best in FIGS. 3 and 4, the cutting blade 108 is a curved sickle-like member having a sharp proximal end 120, a dull convex edge 122, a sharp concave edge 124, and a distal end 126 which is coupled to the distal end 128 of the push rod 104. According to a preferred embodiment of the invention, the deflecting surface 112 is a cylindrical guide channel which is inclined in the distal direction and intersects the radial slot 110 in a radial hole 111 which is distally adjacent to the slot 110 as seen best in FIG. 5. The cylindrical guide channel 112 is provided with a proximal lateral opening 113 extending along substantially its entire length and dimensioned to admit the distal end 128 of the push rod 104 and the distal end 126 of the cutting blade 108. The distal ends of the cutting blade and the push rod are coupled to each other via a substantially cylindrical piston-like member 130 which slides in the guide channel 112. The piston-like member 130 may be formed as part of the blade 108, part of the push rod 104, or may be a separate member which is glued, welded or otherwise affixed to the blade and the push rod.

Figures 1, 2:
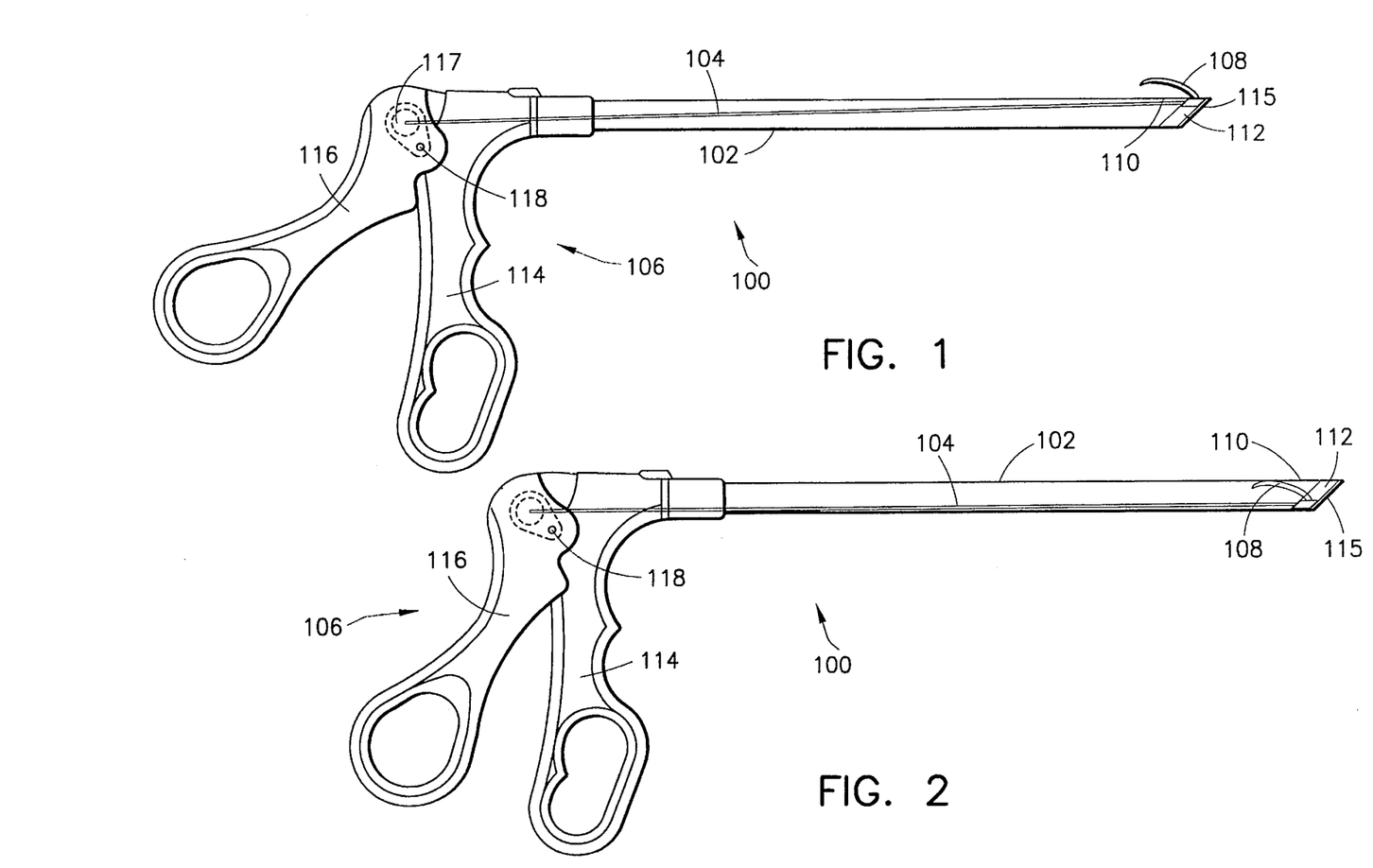
FIG. 1 a partially transparent side elevation view of an endosurgical instrument having a retractable sickle blade according to the invention with the blade deployed.
FIG. 2 a view similar to FIG. 1 with the blade retracted.

When the push rod 104 is in the proximal position as shown in FIGS. 2 and 3, the cutting blade 108 is substantially completely contained within the tube 102 in a "retracted" position. When the push rod 104 is moved distally, the distal end of the push rod urges the piston-like member 130 up through the inclined guide channel 112. The cutting blade 108 is thus moved out of the tube 102 through the radial slot 110 as it is also moved somewhat distally to a "deployed" position as shown in FIGS. 1 and 4. It will be appreciated that the movement of the cutting blade and the push rod is limited in several ways. For example, movement of the push rod 104 is limited by its length and diameter as well as by the rotational movement of the lever 116 (FIGS. 1 and 2). Movement of the blade 108 is thereby limited by the limited movement of the push rod.

It will also be appreciated that as shown, the tube 102 has a distal end 115 which exhibits an angled planar surface which is substantially parallel to the axis of the guide channel 112. Such a distal end surface may be useful in deflecting tissue away from the slot 110 when the instrument is moved distally. However, it is within the scope of the invention to provide any type of surface at the exterior distal end of the instrument. Those skilled in the art will appreciate that other end surfaces such as hemispherical, conical, frustroconical, etc. may provide other desirable effects without interfering with the operation of the instrument.

The embodiment of FIGS. 1–5 may be assembled as follows: The tube 102 is provided with an open end 115 in addition to the radial slot 110 and a radial hole 111 at the distal end of the slot 110. The blade 108, piston-like member 130, and the push rod 104 are assembled and inserted into the distal end 115 of the tube 102. The piston-like member 130 is aligned with the radial hole 111, and the cylindrical guide channel 112 is inserted into the radial hole 111. The distal end 115 of the tube 102 is sealed with epoxy or the like which also maintains the channel 112 securely at the distal end of the tube.

Figure 6:
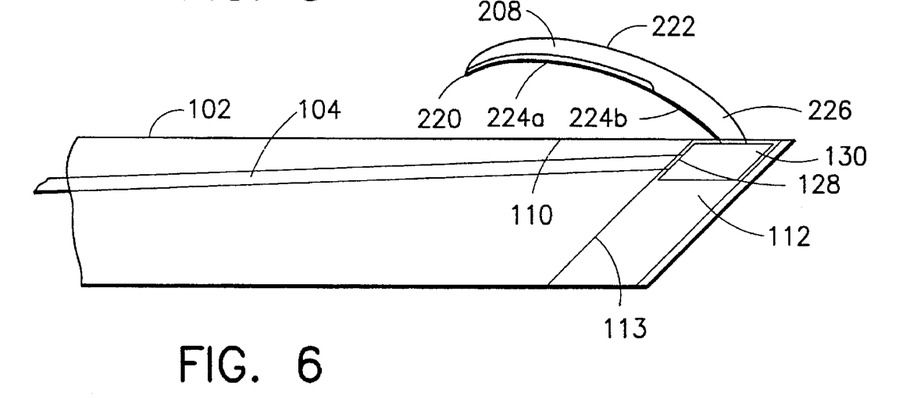
FIG. 6 is a view similar to FIG. 4 of a second embodiment of the endosurgical instrument.
Figures 7, 8:
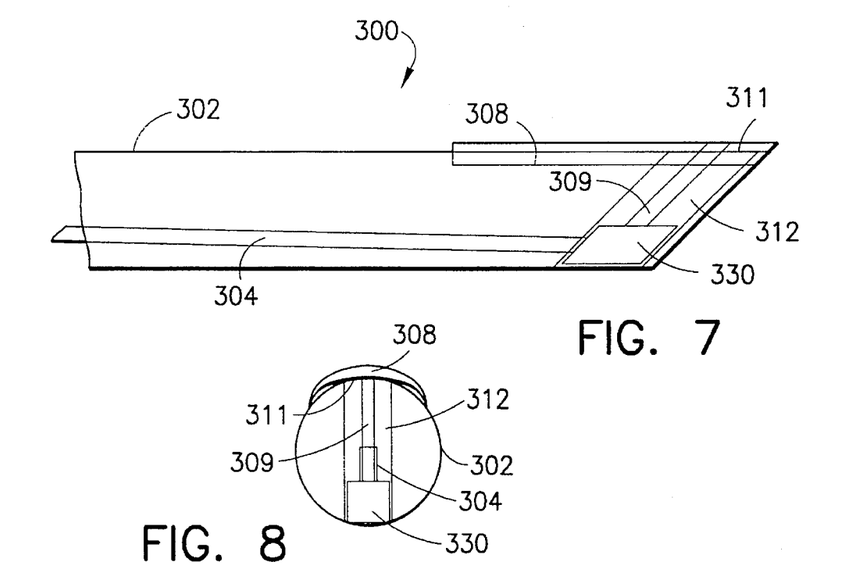
FIG. 7 is a view similar to FIG. 3 of a third embodiment of the invention.
FIG. 8 is a partially transparent distal end view of the instrument of FIG. 7.
Figure 9:
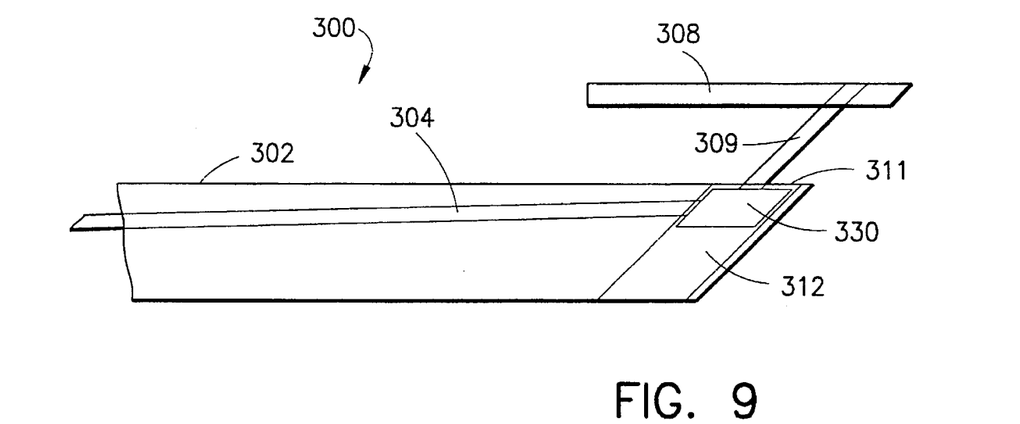
FIG. 9 is a view similar to FIG. 4 of the third embodiment of the invention.
Figure 10:
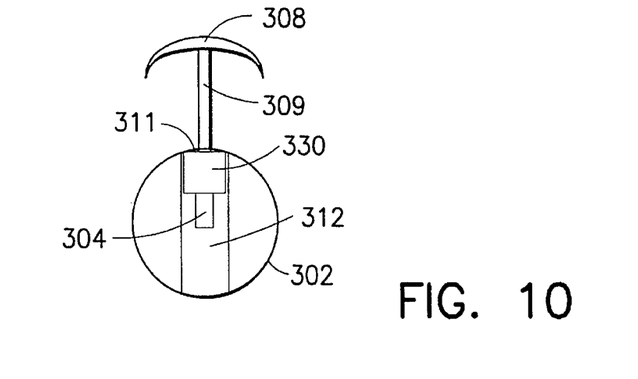
FIG. 10 is a partially transparent distal end view of the instrument of FIG. 9.
Figure 11:
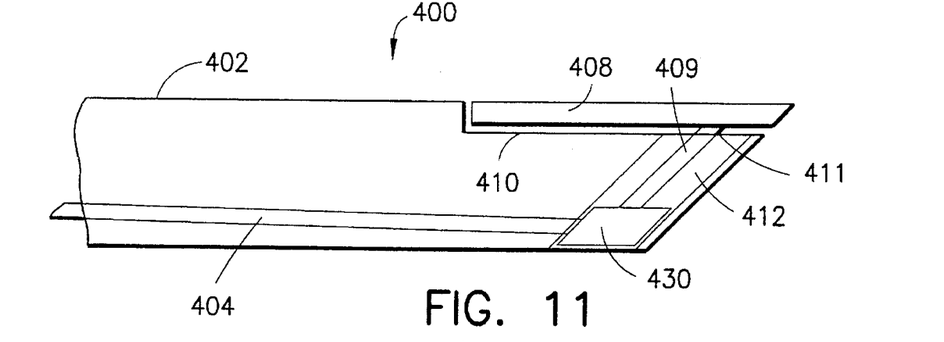
FIG. 11 is a view similar to FIG. 3 of a fourth embodiment of the invention.
Figure 12:
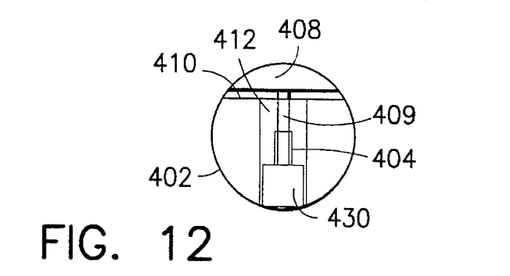
FIG. 12 is a partially transparent distal end view of the instrument of FIG. 11.
Figure 13:
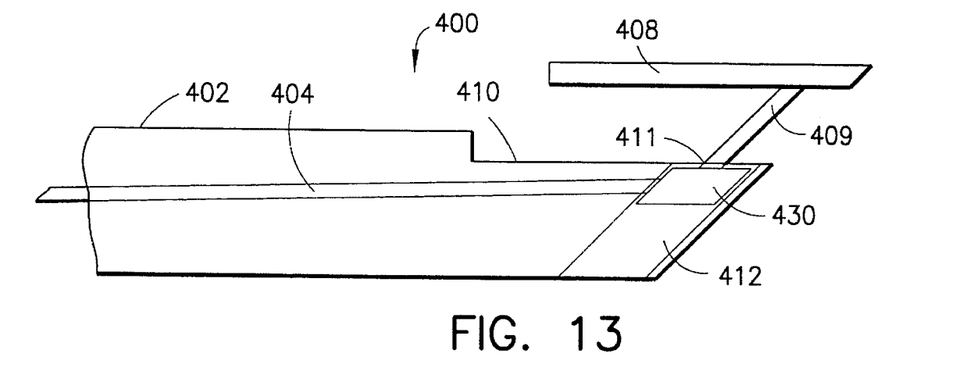
FIG. 13 is a view similar to FIG. 4 of the fourth embodiment of the invention.
Figure 14:
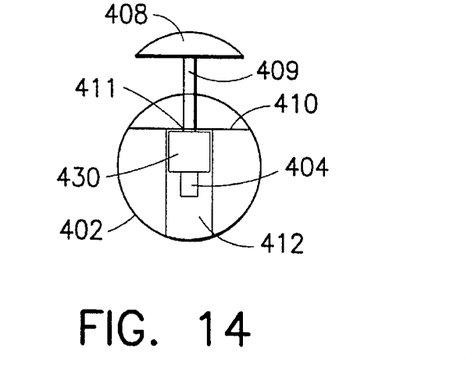
FIG. 14 is a partially transparent distal end view of the instrument of FIG. 13.
Figure 15:
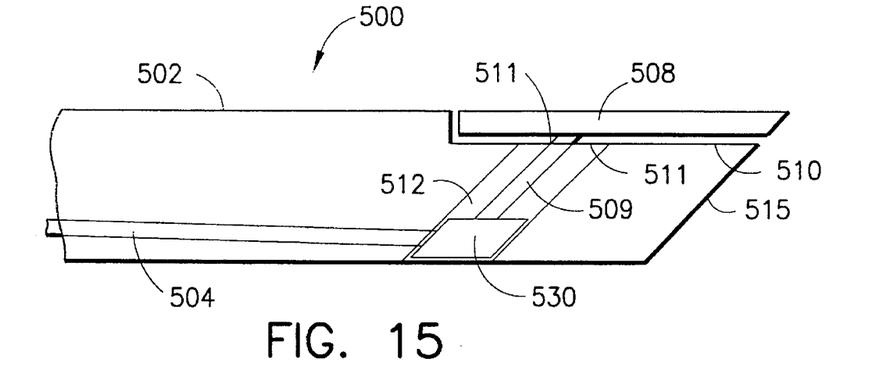
FIG. 15 is a view similar to FIG. 3 of a fifth embodiment of the invention.
Figure 16:
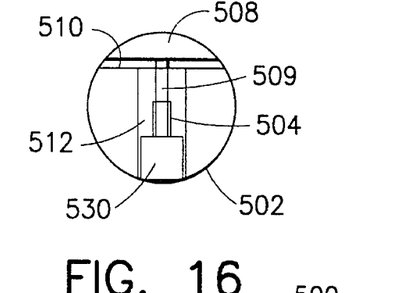
FIG. 16 is a partially transparent distal end view of the instrument of FIG. 15.
Figure 17:
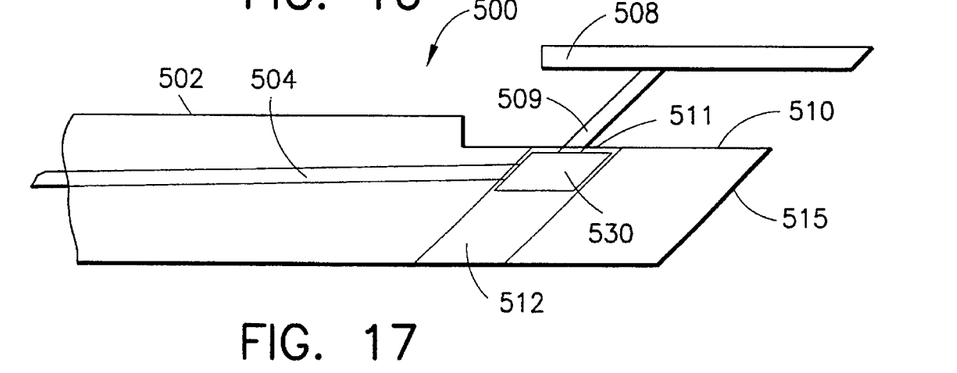
FIG. 17 is a view similar to FIG. 4 of the fifth embodiment of the invention.
Figure 18:
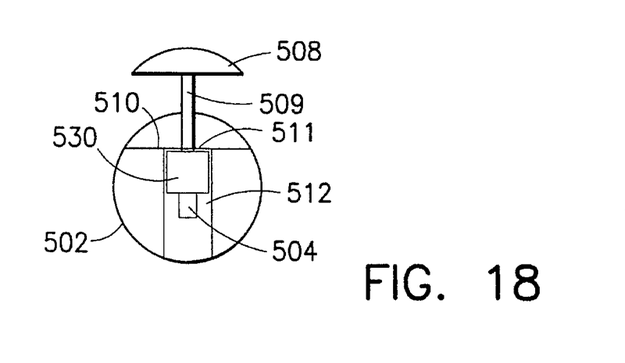
FIG. 18 is a partially transparent distal end view of the instrument of FIG. 17.

FIG. 6, shows an alternate embodiment of a cutting blade 208 which has a sharp proximal end 220, a dull convex edge 222, a concave edge 224a, 224b, and a distal end 226.

According to this embodiment, the concave edge has a sharp proximal portion 224a and a dull distal portion 224b. The purpose of the dull portion 224b is to allow the instrument to gently move a tissue, vein, duct, or other structure (not shown). Thus, with an object so engaged between the slot 110 and the dull portion 224b of the blade 208, the object can be pulled to a location away from any adjacent tissue, where positive identification by imaging or other equipment can be achieved. When the encompassed object is identified, and cutting of the object is desired, the cutting operation with the sharp cutting portion 234a of the blade 308 proceeds by retracting the blade 208 in the slot 110.

According to preferred aspects of the invention, the tube 102 and the push rod 104 are made of stainless steel and the cutting blade 108 is a cobalt base alloy as disclosed in co-owned U.S. Pat. No. 5,234,453 which is incorporated by reference herein. The tube 102 preferably has a diameter of approximately 0.176" and the push rod 104 preferably has a diameter of approximately 0.060". The slot 110 is preferably configured to act as a shearing edge relative to the sharp edge 124 (224a) of the blade 108 (208). The guide channel 112 is preferably inclined at an angle of approximately 60°. According to a presently preferred embodiment, the convex edge 122 (222) of the cutting blade 108 (208) has a radius of curvature of approximately 0.375" and the concave edge 124 (224) has a radius of curvature of approximately 0.250".

From the foregoing, it will be appreciated that the inclined deflection surface according to the invention may be used with an end effector other than a cutting blade. For example, the end effector may take the form of a gripper/dissector as shown in FIGS. 7–18.

Turning now to FIGS. 7–10, an endosurgical gripping/dissecting instrument 300 according to the invention is similar to the cutting instruments described above having a hollow tube 302 and a push rod 304 extending therethrough. Those skilled in the art will appreciate that the proximal ends of the tube and the push rod are coupled to an actuator handle such as the one shown in FIGS. 1 and 2. The tube 302 is provided with a distal inclined deflection surface, in this case an inclined cylindrical channel 312, and the distal end of the push rod 304 engages the deflection surface, in this case by means of a cylindrical piston-like member 330. The tube 302, in this embodiment of the invention, is provided with a radial hole 311 adjacent to the channel 312, but no radial slot is necessary. A gripper/dissector 308 is formed as a hollow cylinder segment and is coupled to the piston-like member 330 by an extension arm 309. When the instrument is in the retracted position shown in FIGS. 7 and 8, the gripper/dissector 308 substantially embraces the upper distal surface of the tube 302. When the push rod 304 is moved distally, the piston-like member 130 engages the inclined guide channel 312 and moves upward toward the hole 311 in the tube 302. The extension arm 309 rises out of the hole 311 and the gripper/dissector 308 is moved radially and distally from the tube 302 to the deployed position shown in FIGS. 9 and 10. Movement of the push rod 304 in the proximal direction will return the gripper/dissector 308 to the retracted position shown in FIGS. 7 and 8.

FIGS. 11–14 show another endosurgical gripping/dissecting instrument 400 according to the invention. The gripping/dissecting instrument 400 is similar to the instrument 300 described above and similar reference numerals refer to similar parts of the instrument. The instrument 400 differs from the instrument 300 in that a distal portion 410 of the tube 402 is flattened and the gripper/dissector 408 is a solid cylinder segment rather than a hollow one. In the retracted position shown in FIGS. 11 and 12, the gripper/dissector 408 is nested on the flattened portion 410 of the tube 402. In the deployed position shown in FIGS. 13 and 14, the gripper/ dissector 408 is raised above the flattened portion 410 of the tube 402. The operation of the instrument 400 is substantially the same as the operation of the instrument 300.

All of the above instruments have common features, e.g., each has an end effector which is moved radially and distally by the push rod engaging a deflecting surface. In addition, each of the instruments above may be considered to be "retrograde" or backward acting. It will be appreciated, however, that the deflecting surface feature of the invention can be used with an instrument which is forward acting.

FIGS. 15–18 show an embodiment of a gripper/dissector instrument 500 which is similar to the instrument 400 described above and in which similar reference numerals refer to similar parts of the instrument. In the instrument 500, however, the guide channel 512 is located proximally of the distal end 515 of the tube 502. Thus, the space between the gripper/dissector 508 and the flattened part 510 of the tube 502 is open at the distal end of the instrument and not blocked in any way by the extension arm 509, as compared to the extension arm 409 in FIGS. 11–14 which blocks the distal end access to the space between the gripper/dissector 408 and the flattened part 410 of the tube 402. Thus, while the instrument 400 is retrograde in the sense that the end effector 408 must be brought behind the object to be grasped, the instrument 500 is forward acting since the end effector 508 can grasp an object by approaching it from the front.

It should be appreciated that rather than locating the deflecting surface 512 proximally from the distal end 515 of the tube 502, it is possible to incline the deflecting surface in the proximal direction as opposed to the distal direction as shown. If the deflecting surface is inclined in the proximal direction, the end effector will be deployed when the push rod is moved proximally and will be retracted when the push rod is moved distally. Therefore, it may be desirable to reverse the components 114, 116 of the handle actuator 106 (FIGS. 1 and 2) if it is desired that the end effector retract when the handle actuator is squeezed. Also, rather than coupling the end effector to the push rod at the location of the deflection surface, it is possible to locate the end effector to rod connection proximally of the deflection surface. In this case, the slot or hole in the tube must be provided at the end effector to rod connection location rather than at the deflection surface location.

There have been described and illustrated herein several embodiments of endosurgical instruments having inclined distal deflection surfaces for moving an end effector both radially and distally. While particular embodiments of the invention have been described, it is not intended that the invention be limited thereto, as it is intended that the invention be as broad in scope as the art will allow and that the specification be read likewise. Thus, while particular materials and dimensions have been disclosed, it will be appreciated that other materials and dimensions may be used to achieve similar results. Also, while a sickle shaped cutting blade has been disclosed, another shaped blade may be used. In addition, while several different gripper/dissector end effectors have been shown, it will be appreciated that other types of grippers/dissectors can be used. Furthermore while a particular handle actuator has been disclosed, it will be understood other actuating means can be used. Moreover, while particular configurations have been disclosed with reference to the inner deflecting surface it will be appreciated that other configurations could be used as well. In addition, while the cutting or gripping member has been shown to be coupled to the distal end of the push rod, it could be coupled to the push rod at a point proximal of the distal end. It will therefore be appreciated by those skilled in the art that yet other modifications could be made to the provided invention without deviating from its spirit and scope as so claimed.

We claim:

1. An endosurgical instrument, comprising:
   a) a hollow tube having a proximal end, and a distal end, and a wall defining a radial opening near said distal end;
   b) a push rod having a proximal end and a distal end, said push rod extending at least partially through said hollow tube;
   c) a deflecting surface inside said hollow tube and near said distal end of said hollow tube;
   d) a non-rotatable end effector coupled to said push rod with said end effector extending at least partially outside said tube and coupled to said push rod through said radial opening when said end effector is in a deployed position; and
   e) actuation means coupled to said proximal end of said hollow tube and said proximal end of said push rod for effecting a relative axial movement of said tube and push rod, wherein
   relative axial movement of said tube and push rod causes said distal end of said push rod and said deflecting surface to engage such that said end effector is moved radially and distally relative to said tube.

2. An endosurgical instrument according to claim 1, wherein:
   said radial opening includes a radial slot, and said end effector is a cutting blade.

3. An endosurgical instrument according to claim 2, wherein:
   said cutting blade has a sharp edge and a dull edge, said sharp edge facing proximally and radially inward relative to said push rod.

4. An endosurgical instrument according to claim 3, wherein:
   said cutting blade is curved.

5. An endosurgical instrument according to claim 2, wherein:
   said cutting blade is sickle shaped and has an inner edge and an outer dull edge, said inner edge further has a distal dull portion and a proximal sharp portion.

6. An endosurgical instrument according to claim 1, wherein:
   said deflecting surface is substantially cylindrical.

7. An endosurgical instrument according to claim 6, wherein:
   said deflecting surface is inclined in the distal direction.

8. An endosurgical instrument according to claim 1, wherein:
   said actuation means comprises a handle coupled to said proximal end of said tube and a lever pivotally coupled to said handle and coupled to said proximal end of said push rod.

9. An endosurgical instrument according to claim 1, wherein:
   said distal end of said tube has a tapered outer surface.

10. An endosurgical instrument according to claim 1, wherein:
    said deflecting surface is a substantially cylindrical guide channel having an open end adjacent to said radial opening and a proximal lateral opening.

11. An endosurgical instrument according to claim 10, wherein:
said distal end of said push rod is provided with a substantially cylindrical piston-like member which slides in said guide channel.

12. An endosurgical instrument according to claim 1, wherein:
said end effector is a gripper/dissector.

13. An endosurgical instrument according to claim 12, wherein:
said gripper/dissector is formed as a segment of a hollow cylinder which embraces said tube when said end effector is moved to a retracted position.

14. An endosurgical instrument according to claim 12, wherein:
a distal portion of said tube is flattened and said gripper/dissector is formed as a segment of a solid cylinder which nests on said flattened portion of said tube when said end effector is moved to a retracted position.

15. An endosurgical instrument according to claim 12, wherein:
said deflecting surface is a substantially cylindrical guide channel having an open end adjacent to said radial opening and a proximal lateral opening.

16. An endosurgical instrument according to claim 15, wherein:
said distal end of said push rod is provided with a substantially cylindrical piston-like member which slides in said guide channel.

17. An endosurgical instrument according to claim 16, wherein:
said gripper/dissector is coupled to said substantially cylindrical member by an extension arm which extends through said radial opening.

18. An endosurgical instrument according to claim 1, wherein:
said end effector is substantially rigidly coupled to said distal end of said push rod.

19. An endosurgical instrument, comprising:
a) a hollow tube having a proximal end, and a distal end, and a wall defining a radial opening near said distal end;
b) a push rod having a proximal end and a distal end, said push rod extending at least partially through said hollow tube;
c) a deflecting surface inside said hollow tube and near said distal end of said hollow tube;
d) an end effector coupled to said push rod with said end effector extending at least partially outside said tube and coupled to said push rod through said radial opening when said end effector is in a deployed position; and
e) actuation means coupled to said proximal end of said hollow tube and said proximal end of said push rod for effecting a relative axial movement of said tube and push rod, wherein relative axial movement of said tube and push rod causes said distal end of said push rod and said deflecting surface to engage such that said end effector is moved in a straight line radially and distally relative to said tube.

20. An endosurgical instrument, comprising:
a) a hollow tube having a proximal end, and a distal end, and a wall defining a radial opening near said distal end;
b) a push rod having a proximal end and a distal end, said push rod extending at least partially through said hollow tube;
c) a deflecting surface inside said hollow tube and near said distal end of said hollow tube;
d) an end effector coupled to said push rod with said end effector extending at least partially outside said tube and coupled to said push rod through said radial opening when said end effector is in a deployed position; and
e) actuation means coupled to said proximal end of said hollow tube and said proximal end of said push rod for effecting a relative axial movement of said tube and push rod, wherein relative axial movement of said tube and push rod causes said distal end of said push rod and said deflecting surface to engage such that said distal end of said push rod is moved in a straight line which is angled relative to the longitudinal axis of said tube and said end effector is moved radially and distally relative to said tube.

* * * * *